United States Patent [19]

Howell et al.

[11] Patent Number: 5,139,946

[45] Date of Patent: Aug. 18, 1992

[54] DOT MATRIX MEMBRANE CELL EXPANSION

[75] Inventors: Gary W. Howell, Elkton, Md.; Joseph D. Irr, Newark; Ara T. Nahapetian, Wilmington, both of Del.

[73] Assignee: Du Pont Merck Pharmaceutical Company, Wilmington, Del.

[21] Appl. No.: 725,148

[22] Filed: Jul. 9, 1991

Related U.S. Application Data

[62] Division of Ser. No. 266,876, Nov. 2, 1988, Pat. No. 5,068,195.

[51] Int. Cl.$^5$ .................. C12N 5/06; C12N 5/08; C12N 5/04; C12N 1/00
[52] U.S. Cl. .................. 435/240.2; 435/240.23; 435/240.241; 435/240.4; 435/243; 435/818
[58] Field of Search .............. 435/1, 140.1, 240.2, 435/240.23, 240.24, 240.241, 240.243, 240.25, 240.26, 240.27, 240.4, 243, 283–286, 311, 313, 818

[56] References Cited

U.S. PATENT DOCUMENTS

| | | | |
|---|---|---|---|
| 3,642,047 | 2/1972 | Waage | 128/272 |
| 3,911,140 | 10/1975 | Osborne et al. | 426/36 |
| 4,140,162 | 2/1979 | Gajewski et al. | 260/45.75 |
| 4,191,231 | 3/1980 | Winchell et al. | 128/272 |
| 4,201,845 | 5/1980 | Feder et al. | 435/285 |
| 4,242,460 | 2/1980 | Chick et al. | 435/284 |
| 4,308,351 | 12/1981 | Leighton et al. | 435/285 |
| 4,391,912 | 7/1983 | Yoshida et al. | 435/284 |
| 4,460,365 | 7/1984 | Ganshirt et al. | 604/408 |
| 4,460,366 | 7/1984 | Shinno | 604/408 |
| 4,496,361 | 1/1985 | Kilkson | 604/408 |
| 4,516,977 | 5/1985 | Herbert | 604/408 |
| 4,588,401 | 5/1986 | Kilkson | 604/408 |
| 4,661,455 | 4/1987 | Hubbard | 435/284 |
| 4,734,372 | 3/1988 | Rotman | 435/291 |
| 4,748,124 | 5/1988 | Vogler | 435/285 |
| 4,839,046 | 6/1989 | Chandler | 435/311 |
| 4,839,296 | 6/1989 | Kennedy et al. | 436/170 |
| 4,851,210 | 7/1989 | Hewett | 422/57 |

OTHER PUBLICATIONS

Feder et al. "Mass-Culture of Mammalian Cells in Perfusion Systems", ABL. (Jan./Feb. 1985), pp. 24–36.
Nahapetian, "Growth Maintenance of Anchorage-Dependent Mammalian Cells in Perfused Systems and Metabolism of Nutrients", Chapter 7, Mammalian Cell Technology, (Beton, Butterworth, 1986), pp. 151–165.

*Primary Examiner*—Robert J. Warden
*Assistant Examiner*—William H. Beisner
*Attorney, Agent, or Firm*—Margaret Horn; Blair Q. Ferguson

[57] ABSTRACT

There is disclosed a perfusable cell culture device capable of expansion and maintenance of biological cells, including mammalian, microbial, plant and insect cells in culture. The device comprises an upper and lower polymeric film layer and a gas and liquid permeable flow divider membrane. The flow divider membrane is affixed between the upper and lower polymeric layers and to the lower polymeric layer in a manner providing channels for fluid distribution of culture medium which is perfused at a controlled rate, uniformly across the flow divider membrane and to a bed of cells dispersed on the flow divider membrane.

8 Claims, 2 Drawing Sheets

DOT MATRIX MEMBRANE CELL EXPANSION

This is a division of application Ser. No. 07/266,876, filed Nov. 2, 1988, now U.S. Pat. No. 5,068,195.

BACKGROUND OF THE INVENTION

This invention relates to a perfusable cell culture device, and more particularly comprises a flow divider membrane attached to a lower polymeric layer in a manner which provides channels for uniform fluid distribution over the entire surface of the flow divider membrane and into a bed of cells dispersed thereon.

Early in the history of tissue culture a need to perfuse culture systems was recognized. As early as 1912, attempts to furnish cultures of animal cells with a continuous supply of fresh nutrient medium were made. Feder, J., Tolbert, W. R. *Mass Culture of Mammalian Cells in Perfusion Systems*, ABL, Jan./Feb. 1985, p. 24-36. Since these early attempts, development of perfusion systems has continued and advanced significantly. For a good analysis of the development of perfused systems used for examination of mammalian cells see: Nahapetian, A. T. (1986). "Growth and Maintenance of Anchorage Dependent Mammalian Cells in Perfused Systems and Metabolism of Nutrients", Chapter 7, *Mammalian Cell Technology*, W. G. Thilly(ed), pp. 151-165, Buttersworth, Boston.

Conventional cell culture systems incorporate a membrane or membranes used to diffuse either nutrients, metabolic waste, gases or cellular products into or out of the cell's environment. For example, U.S. Pat. No. ,4,308,351 Leighton et. al. describes an apparatus comprising encasing a tissue sample attached to a membrane and a support for the membrane, in a specially designed closed container filled with solution and then bathed in a nutrient solution. Due to a designed nutrient concentration gradient occurring in the tissue, the tissue sample receives oxygen and nutrients by diffusion through the membrane from the nutrient bath as the membrane is exposed to the bath through apertures in the closed container. U.S. Pat. No. 3,911,140 Osborne et. al. describes a fermenter in which a dialysis membrane separates a culture medium containing propagating microorganisms from a regenerating solution containing nutrients. The dialysis membrane is impermeable to the microorganisms and allows diffusion of desired nutrients based on a concentration gradient of nutrients and lactic acid on either side of the membrane. Contrary to the conventional art, the present invention incorporates a flow divider membrane which due to the manner in which it is affixed to the lower polymeric layer, allows for uniform distribution of culture medium over the entire flat surface of the flow divider membrane, rather than incorporating a filter to control diffusion of nutrients, metabolic waste, gases or cellular product between varying sides of a concentration gradient.

The present invention provides a device designed to perfuse cells during culture which is capable of providing a favorable environment for expansion and maintenance of both anchorage dependent (in combination with microcarriers) and anchorage independent cells, such device having the following characteristics: 1) it provides continuous supply of nutrients and continuous removal of metabolic end products; 2) it provides adequate $O_2$ and $CO_2$ exchange with the surrounding environment; 3) it maintains a favorable pH by gas exchange; 4) it is designed such that the nutrients flow uniformly through the cell bed, independent of diffusion gradients or thermal agitation; 5) it is transparent thereby allowing visual examination of the culture and additionally allowing light to pass through the vessel thereby providing an essential environment when the device is used for plant cells; 6) it equilibrates temperature easily with the surrounding environment; 7) it exerts no shear, since there is no need for constant mixing of the culture; 8) it provides a sterile environment; 9) it is non-breakable, disposable or sterilizable by autoclave; 10) it is not bulky and can be stacked on on top of another when not in use, therefore conserving space; and 11) it is more cost effective than other perfused vessels available on the market.

SUMMARY OF THE INVENTION

The invention is a disposable, sterile, plastic container useful as a perfusable cell culture device for biological cells including mammalian, microbial, plant and insect cells in culture. The device is structured such that there are two liquid impermeable polymeric sheets, each capable of transferring oxygen and carbon dioxide at rates sufficient to maintain cells in culture, hereinafter referred to as the upper and lower polymeric layers, which are joined together at their peripheral edges in a sealing manner. Between the upper and lower polymeric layers and affixed to the lower polymeric layer is a gas and liquid permeable flow divider membrane. This flow divider membrane is affixed to the lower polymeric layer with an evenly spaced pattern of seals. The two are affixed such that the pressure drop across the flow divider is significantly greater than the pressure drop through the channels created between the seals. Thus, substantially even pressure is provided across the flow divider membrane, allowing culture medium to flow uniformly over a large flat surface area. The culture medium is introduced into these channels at a controlled rate and uniformly flows through the channels and over the entire surface of the cell divider membrane. The device provides for culture medium to be introduced through an inlet port in the lower polymeric layer. The culture medium flows between the lower polymeric layer and the flow divider membrane through the channels for fluid distribution and into a chamber created between the upper polymeric layer and the flow divider membrane. The cells to be cultured are dispersed across the surface of the flow divider membrane and are perfused at a controlled rate with culture medium. A port in the upper polymeric layer acts as a means to place cells into the device, a means to remove cultured cells, and a means for collecting perfused nutrients from the device.

DETAILED DESCRIPTION

Figure 1:
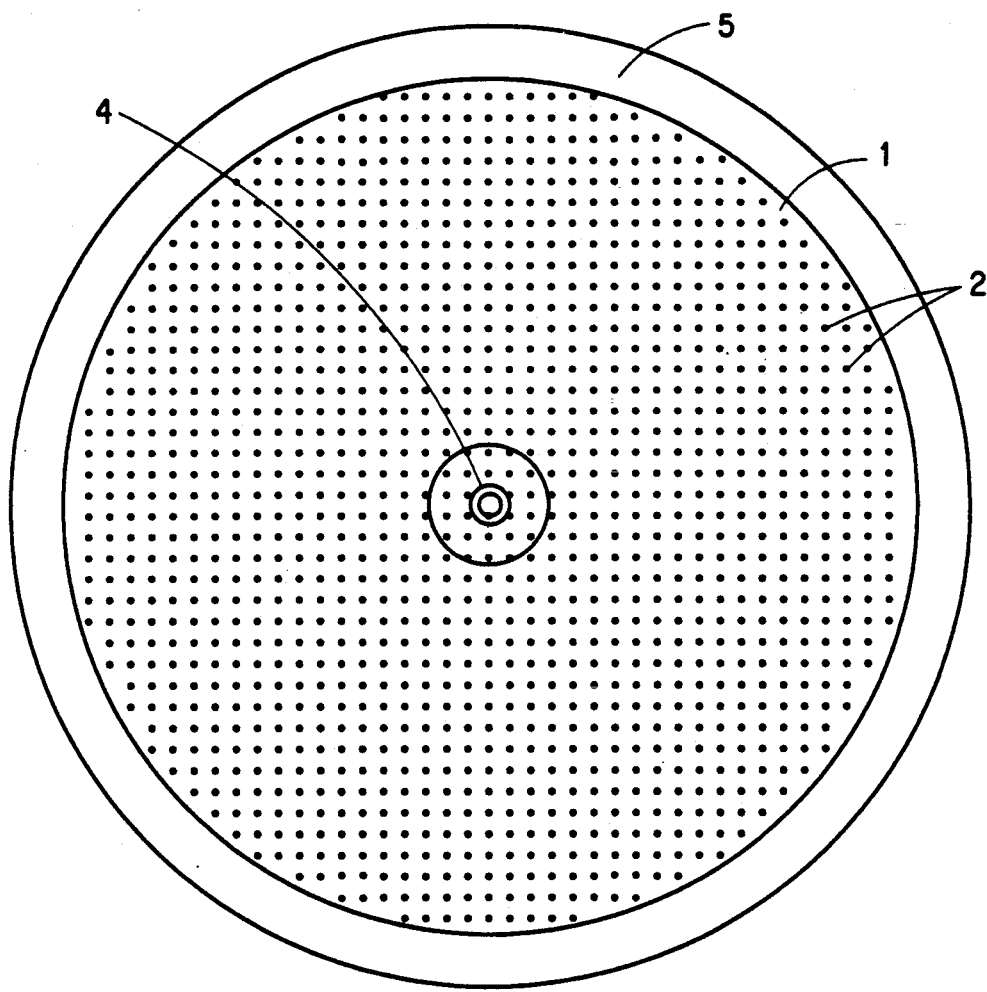
FIG. 1 is a plane view schematically showing a preferred embodiment of a dot matrix pattern of seals joining the lower polymeric layer and the flow divider membrane.
Figure 2:
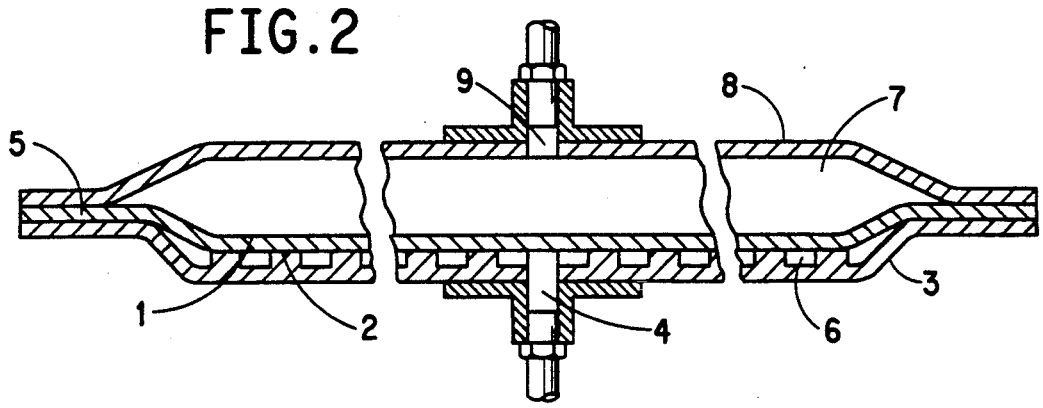
FIG. 2 is an enlarged schematic cross-section of the cell culture device.
Figure 3:
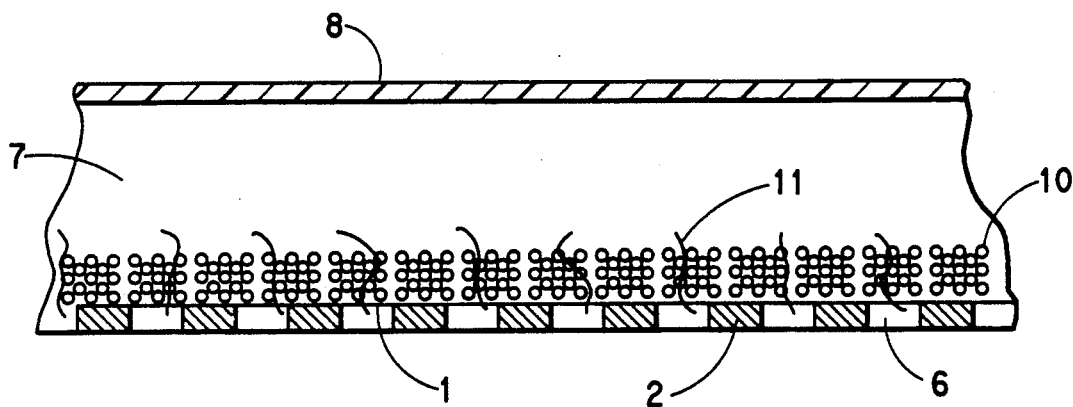
FIG. 3 is an enlarged cross sectional view of the flow divider membrane shown in FIG. 2 with channels for fluid distribution.
Figure 4:
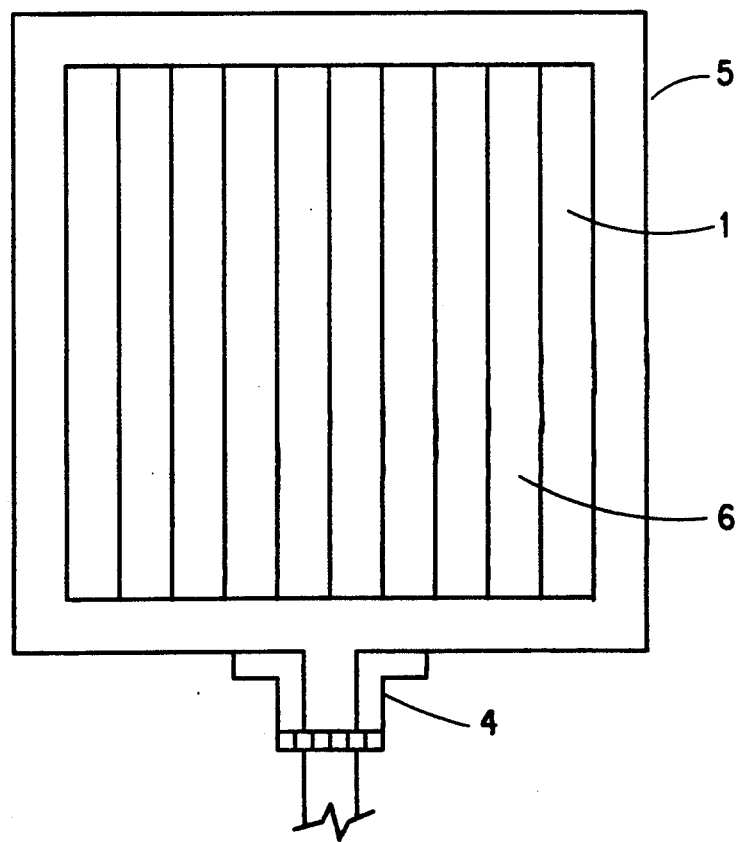
FIG. 4 is a plane view schematically showing an alternate embodiment of an evenly spaced pattern of seals joining the lower polymeric layer and the flow divider membrane.

The flow divider membrane 1 shown in FIGS. 1, 2 and 3 made of a gas and liquid permeable material is joined to a lower polymeric layer 3 shown in FIG. 2, preferably in a dot matrix pattern 2 shown in FIGS. 1, 2 and 3. As viewed in the cross-sectional positions of FIGS. 2 and 3 the seals of the dot matrix pattern 2, used to join the flow divider membrane 1 to the lower polymeric layer 3, provide channels for fluid distribution 6. Access of culture medium 11, to the channels for fluid distribution 6, is provided through the inlet port 4.

The upper and lower polymeric layers, 8 and 3 respectively, are made of material which is liquid impermeable and permeable to oxygen and carbon dioxide at rates sufficient to maintain cells in culture. The peripheral edges 5 of the upper and lower polymeric layers, 8 and 3 respectively, are joined in a sealing manner.

As viewed in FIG. 1, a dot matrix pattern 2, in which the flow divider membrane 1 is attached to the lower polymeric layer 3, preferably has a mean pore size between 0.45 μm and 1.0 μm in diameter.

The flow divider membrane 1, is preferably made of expanded polytetrafluoroethylene (PTFE) material, commercially available as Gore-tex ®. Uniform distribution of fluid through the flow divider membrane 1 occurs because the pressure drop over the surface of the flow divider membrane 1 is significantly greater than the pressure through the channels 6, which are formed by the seals of the dot matrix pattern 2. The significantly greater pressure drop across the surface of the flow divider membrane 1, compared to the pressure in the channels for fluid distribution 6 allows for even pressure across the entire surface of the flow divider membrane and therefore the culture medium is uniformly distributed across the flow divider membrane. As used herein, uniformly means that the center and the outer edge or any other location on the flow divider membrane are to get the same flow rate per unit area, with no gross variation. By affixing the flow divider membrane to the lower polymeric layer in a dot matrix or similar evenly spaced pattern, the pressure between the flow divider membrane and the lower polymeric layer places the spaces between the dot matrix seals at essentially tensile load, thereby maintaining a substantially flat surface. As used herein tensile load means the greatest perpendicular stress a substance can bear without tearing apart. The closer the seals are to each other in the pattern, the closer to tensile load the surface becomes and therefore the flatter the surface is maintained.

In use, the cells to be cultured are placed onto the surface of the flow divider membrane 1, through a port 9 in the upper polymeric layer 8. Culture medium is then perfused through the port 4 in the lower polymeric layer, into the channels for distribution 6 which provide for uniform distribution of the culture medium over the entire surface of the flow divider membrane 1 and through the bed of cells 10. Spent culture medium and products of culture can then be removed through the port 9 in the upper polymeric layer 8. A sterile environment must be maintained within the device therefore a sterile connection system such as Sterile Connection Device ™, commercially available from E. I. DuPont de Nemours Co., is preferably used at the port in the upper polymeric layer, connecting tubing leading from the port to additional tubing, syringe or other object used for adding cells, withdrawing cells or spent culture medium. Such a connection device allows for manipulation of the cell culture device without losing the sterile environment within the device.

A preferred embodiment of this invention includes using expanded PTFE, commercially available as Gore-Tex ®, with a pore size between 0.45 micron and 1.0 micron and preferably 0.45 micron, for the flow divider membrane. Untreated PTFE material is highly hydrophobic to the extent that 0.45 micron pore size untreated PTFE material will pass no measurable volume of aqueous solution with a pressure differential of 5 PSI. Treating the PTFE with a water soluable polymer, such as polyvinylpyrollidone (PVP), solubilized in methanol or other wetting agent, decreases the water contact angle and permits the largest pores to be accessed when if untreated they would be inaccessible to water. Since the PTFE is hydrophobic and the PVP is hydrophilic, it is reasonable to expect a certain amount of PVP or other water soluble polymer, deposited on the PTFE fibers would leave the material weakly hydrophobic or more hydrophilic so as to lessen water entry pressure. Treating PTFE with a specific concentration of PVP/methanol allows an aqueous flow of approximately 200 micro liters per minute at 5 PSI on a surface area of approximately 15 square inches with a pore size of 0.45 micron. A greater concentration of PVP/methanol provides for increased flow at a constant 5 PSI or decreased pressure at 200 micro liters per minute. The effects of flow and pressure changes with expanded PTFE are the result of surface tension changes and not changes in pore size. Increased pressure with the same concentration of PVP/methanol accesses smaller pores for increased flow. Furthermore, increased concentrations of PVP/methanol provide a lower surface tension of smaller pores for increased flow at a constant pressure. Thus a further preferred embodiment of this invention would include taking advantage of the PVP/Methanol affect by tailoring a particular flow divider pore size to divide evenly (via a desired pressure drop), with a desired flow rate. For example 0.45 micron PTFE material can be treated with varying concentrations of PVP/Methanol for 200 micro liter flow at 3 PSI or 500 micro liter at 3 PSI. Although expanded PTFE is a preferred material for the flow divider membrane, other microporus membrane materials such as Nucleopore ® may be used. Nucleopore ®, like expanded PTFE, is made hydrophilic by treatment with a solution of PVP or other water soluble polymer and methanol or other wetting agent.

A preferred method of treating expanded PTFE fibers such as Gore-Tex ®, comprises solubilizing PVP powder in methanol which serves as a wetting agent and vehicle for the PVP into the expanded PTFE fibers. The PVP/methanol solution is then applied to the expanded PTFE fibers, this application can be by immersion or spraying while allowing for air drying of the methanol. Preferably, the application is by controlled immersion and forced air drying such as by mechanically driven rollers. After drying, an amount of PVP will deposit on the expanded PRFE fibers leaving the material weakly hydrophobic or more hydrophilic. Once the PTFE fibers are made more hydrophilic, water can penetrate the material, this condition will remain as long as water is present and the material is not allowed to dry out. The designed flow characteristics of the PVP/methanol treated expanded PTFE fibers will remain after the water soluble PVP has solubilized and flushed away.

Preferred embodiments of this invention include using a PVP/methanol solution particularly since PVP is relatively innocuous to cells used in the device. However, other water soluble polymers such as polyethylene glycol, polyvinyl alcohol or hydroxyethylmethacrylate are useful to render microporous membrane material such as expanded PTFE material more hydrophilic. Methanol is a preferred wetting agent/vehicle for the water soluble polymer. Other wetting agents/vehicles such as ethanol, isopropyl alcohol, acetone, water, glycols or chlorinated solvents are useful.

A preferred embodiment of this invention includes thermally bonding the flow divider membrane to the lower polymeric layer. A further preferred embodiment of this invention includes thermally bonding the flow divider membrane to the lower polymeric layer in a dot matrix pattern. Although thermal bonding is preferred, other methods of affixing the flow divider membrane to the lower polymeric layer such as bonding with adhesive or mechanically staking the two, can be used.

The rate of liquid flow through the device is important to this invention. Uniform flow division is conditional on having appropriate liquid flow to provide the selected back pressure across the population of cells of interest, while not over pressurizing the flow divider and packaging seals. If the back pressure is not attained, the liquid will bias through the center region of the divider and not flow uniformly across the divider. An embodiment of this invention includes liquid flow of between 100 and 500 micro liters per minute when a 5 inch diameter vessel is used. Liquid flow rate will vary based on the unit area of the vessel used.

Polymeric film material suitable for constructing the cell culture device should be liquid impermeable and permeable to oxygen and carbon dioxide at rates sufficient to maintain cells in culture, such as those set forth in U.S. Pat. No. 4,588,401 issued on May 13, 1986 to Kilkson. Suitable polymeric film material can be selected from but not limited to the group consisting of a copolymer of ethylene and an alpha olefin, such as Sclairfilm ®, polytetrafluoroethylene, commercially available as Teflon ®, fluorinated ethylenepropylene copolymer (FEP) also available as Teflon ®, polyester elastomers, such as Hytrel ® commercially available from E. I. du Pont de Nemours.

Further embodiments of this invention include the addition of one or more additional membranes, such as size exclusion membranes, to be affixed to the upper polymeric layer of the device so that internal separations can take place in order to isolate products which may be produced during cultivation. Uniform flow of culture medium would continue to occur across the flow divider membrane independent of diffusion gradients although such diffusion gradients may be present across the surface of additional membranes optionally affixed to the upper polymeric layer. Any additional membranes affixed to the upper polymeric layer would optionally have separate tubing leading from the additional membrane to an additional outlet port in the upper polymeric layer. This additional tubing and additional outlet port would allow for collection of the separated material.

Further embodiments of this invention include the presence of a pump such as a Multistaltic Pump, commercially available from Haake Buchler, which ideally can pump a settable volume of flow per minute. Such a pump is connected to the inlet port in the lower polymeric layer by tubing. Such tubing may also be connected to the port in the upper polymeric layer. A preferred embodiment of this invention includes a connection device, such as the Sterile Connection Device ™ commercially available from E. I. Du Pont, used at the port in the upper polymeric layer when adding cells, withdrawing culture medium, removing cells or performing other manipulations on the device which could cause loss of the sterile environment. The pump and tubing used in the present invention may be of a known type. In addition, the manner in which this tubing is connected to the port on either the upper or lower layer of the cell culture device may be of a manner known in the art.

The perfusable cell culture device of the present invention provides a novel environment for expansion and maintenance of both anchorage dependent (in combination with microcarriers) and anchorage independent biological cells, including mammalian, microbial, plant and insect cells. The present invention is designed to achieve the highest possible density of cells. A high number of cells can be cultured using this device since the device perfuses oxygen as well as nutrients in the culture medium through the bed of cells. The present invention is particularly useful for culturing mammalian cells such as hybridoma cells (HB47), U937 cells and more particularly tumor infiltrating lymphocytes (TIL) cells and lymphokine activated killer (LAK) cells. Culture medium used in the present invention may be of a known type.

The following examples further illustrate the usefulness of this invention for the cultivation of cells.

EXAMPLE 1

A cell culture vessel was structured with a Gore-Tex ® expanded PTFE flow divider membrane heat sealed by use of a dot matrix pattern to a copolymeric film of polyethylene and linear low density polyethylene commercially available from DuPont Canada as Sclairfilm ® said expanded PTFE material being first treated with PVP solubized in methanol. Application of this solution was in the form of immersion and spraying while allowing for air drying of the methanol. A more preferred and consistent method of application includes forced air drying and controlled immersion such as by mechanically driven rollers.

A concentration of 1 gram PVP to 30 ml methanol yields effective pressure and flow.

The dry expanded PTFE Gore-Tex ®, 0.45 $\mu$ mean pore size, flow divider membrane was bonded to the copolymeric film in a dot matrix pattern by means of a textured heated platen at approximately 300 degrees F, for approximately 5 seconds at approximately 30 PSI. The textured surface, having 0.06 diameter raised dots at 0.125 centers, provides physical connection of the two materials and also channels for fluid distribution between the materials.

Completion of the device less further embodiments and ancillary connector fittings was accomplished by connecting an upper polymeric layer to the previously affixed flow divider membrane and lower polymeric layer, at their peripheral edges. Bonding temperature, pressure, and dwell time is dependent on the materials used. For example, when fluorinated ethylenepropylene copolymer (FEP) commercially available as Teflon ® is used as the upper and lower polymeric layer, the PTFE and FEP bonding temperature is approximately 700 degrees F, for approximately 10 seconds at approximately 40 PSI.

The entire device is schematically represented in FIG. 2.

EXAMPLE 2

The 0.45 $\mu$ vessel of Example 1 was used for the expansion and maintenance of a hybridoma which produces monoclonal antibody to interleukin $-2$ (IL-2). The dot matrix perfused system was maintained by having fresh Iscove's modified DMEM medium perfused at a rate of 250 ml/day. The perfused system was maintained in an incubator containing 5% $CO_2$ in air at 37° C. Cultures were compared to available fed-batch control SteriCell TM cell culture bags (DuPont) having a growth surface area of 150 cm$^2$, which were maintained in the same environment. The following data were taken:

|  | Dot-matrix Perfused | Fed Batch |
|---|---|---|
| Total viable cells (time = 0) | 1.54 × 10$^7$ | 1.54 × 10$^7$ |
| Total viable cells (time = 7 days) | 1.05 × 10$^9$ | 2.78 × 10$^8$ |
| Cell viability (time = 0) | 85% | 85% |
| Cell viability (time = 7 days) | 90% | 77% |
| Viable cell number/cm$^2$ (time = 0) | 1.25 × 10$^5$ | 1.23 × 10$^5$ |
| Viable cell number/cm$^2$ (time = 7 days) | 8.54 × 10$^6$ | 1.85 × 10$^6$ |
| Viable cell number/ml (time = 0) | 2.9 × 10$^5$ | 2.9 × 10$^5$ |
| Viable cell number/ml (time = 7 days) | 1.5 × 10$^7$ | 1.39 × 10$^6$ |
| Number of monocell layers (time = 0) | 0.1 | 0.1 |
| Number of monocell layers (time = 7 days) | 6.83 | 1.48 |

The data show enhancements of perfused versus fed-batch cultures in total cells of 378%, cell viability, 117%; cell number/cm 461%; viable cell number/ml, 1079%; and number of monocell layers 461%.

EXAMPLE 3

U937 cells were used for a comparative study of the cell expansion in a 0.45 $\mu$ dot-matrix perfused vessel of Example 1 and a fed-batch SteriCell TM system (DuPont). The following data were collected:

| U937 CELLS | Perfused Dot-Matrix | Fed-Batch |
|---|---|---|
| Growth surface area, CM2 | 123 | 150 |
| Total viable cell number on day 0 | 8.05 × 10$^7$ | 2.28 × 10$^8$ |
| Total viable cell number on day 24 | 8.91 × 10$^8$ | 5.12 × 10$^8$ |
| Cell viability on day 0 | 69% | 77% |
| Cell viability on day 24 | 84% | 59% |
| Viable cell number per CM2 on day 0 | 7.12 × 10$^5$ | 1.52 × 10$^6$ |
| Viable cell number per CM2 on day 24 | 7.88 × 10$^6$ | 3.41 × 10$^6$ |
| Viable cell number per ml on day 0 | 9.70 × 10$^5$ | 1.14 × 10$^6$ |
| Viable cell number per ml on day 24 | 1.31 × 10$^7$ | 2.56 × 10$^6$ |
| Number of mono-cell-layers on day 0 | 0.57 | 1.22 |
| Number of mono-cell-layers on day 24 | 6.31 | 2.73 |

The data show enhancements of perfused versus fed-batch cultures in total viable cell number 180%, viable cell number/cm$^2$ 400% monocell layers 250%, viability (%) 142%, viable cell number/ml 5000%.

EXAMPLE 4

TIL 714 cells were used for a comparative study of the cell expansion and maintenance in a 0.45 $\mu$ dot-matrix perfused vessel of Example 1 and a fed-batch SteriCell TM system (DuPont). The following data was collected:

| TIL 714 CELLS | Perfused Dot-Matrix | Fed-Batch |
|---|---|---|
| Growth surface area on day 0, CM2 | 121 | 700 |
| Growth surface area on day 10, CM2 | 121 | 5600 |
| Total viable cell number on day 0 | 1.04 × 10$^8$ | 8.55 × 10$^8$ |
| Total viable cell number on day 10 | 1.12 × 10$^9$ | 8.88 × 10$^9$ |
| Cell viability on day 0 | 94% | 93% |
| Cell viability on day 10 | 85% | 86% |
| Viable cell number per CM2 on day 0 | 8.60 × 10$^5$ | 1.22 × 10$^6$ |
| Viable cell number per CM2 on day 10 | 9.26 × 10$^6$ | 1.59 × 10$^6$ |
| Viable cell number per ml on day 0 | 2.30 × 10$^6$ | 1.71 × 10$^6$ |
| Viable cell number per ml on day 10 | 1.87 × 10$^7$ | 2.22 × 10$^6$ |
| Number of mono-cell-layers on day 0 | 0.69 | 0.98 |
| Number of mono-cell layers on day 10 | 7.40 | 1.27 |

EXAMPLE 5

Cells isolated from a normal donor were cultured in a static SteriCell TM bag (DuPont) for three days in serum-free Aim-V medium (Gibco) supplemented with 10 units/ml of recombinant IL-2 (rIL-2). On day 0 all cells from the bag were transferred to a 1.0 $\mu$ dot-matrix vessel of Example 1 which was then perfused with the same rIL-2 supplemented medium for 18 days at a flow rate of 10 ml/hr. On the indicated days LAK cell activity, as measured by $LU_{30}/10^6$ cells, was determined with a four hour $^{51}Cr$ release assay against the human lymphoblastoid cell line Raji. Cell counts, viability, glucose and lactic acid determination were also performed to monitor cell survival and metabolism. The following data were obtained:

| Device | Days | Viability | Total Viable Cells | $LU_{30}/$ 10$^6$ Cells | Total Lytic Units | Glucose [mg/dl] | Lactate [mMolar] |
|---|---|---|---|---|---|---|---|
| Dot Matrix Bag | 0 | 83% | 9.0 × 10$^8$ | 36.8 | 33,000 | 300 | 0 |
|  | 3 | 87% | 3.7 × 10$^8$ | 47.1 | 17,000 | 256 | 4.5 |
|  | 7 | 82% | 5.3 × 10$^8$ | 143.0 | 75,000 | 203 | 9.8 |
|  | 10 | 89% | 5.9 × 10$^8$ | 95.8 | 56,000 | 216 | 8.8 |
|  | 14 | 74% | 6.1 × 10$^8$ | 91.0 | 55,000 | 176 | 13.2 |
|  | 18 | 68% | 7.9 × 10$^8$ | 50.0 | 39,000 | 53 | 13.2 |

Total lytic units = $LU_{30}/10^6$ cells × total viable cells

EXAMPLE 6

Cells from a normal donor were activated in Aim-V medium (Gibco) with 10 units/ml rIL-2 by culture for 3 days in SteriCell TM bags (DuPont) before they were partitioned into two static cultures in SteriCell TM bags (DuPont) at two different concentrations and into a 0.45

μ Dot Matrix vessel of Example 1, perfused at 10 ml/hr. The following data were obtained:

| Device | Days | Viability | Total Viable Cells | $LU_{30}/$ $10^6$ Cells | Total Lytic Units | Glucose [mg/dl] | Lactate [mMolar] |
|---|---|---|---|---|---|---|---|
| SteriCell TM | 0 | 95% | $9.0 \times 10^7$ | 2.1 | 189 | 300 | 0 |
| Bag | 3 | 92% | $4.6 \times 10^7$ | 9.5 | 390 | 284 | 1.8 |
| Low Density | 7 | 94% | $5.8 \times 10^7$ | 59.8 | 2,700 | 242 | .6 |
| Static | 10 | 81% | $7.0 \times 10^7$ | 27.2 | 1,300 | 164 | 13.6 |
| Culture | 14 | 40% | $1.26 \times 10^8$ | 9.0 | 680 | 99 | 19.5 |
| SteriCell TM | 0 | 95% | $9.0 \times 10^8$ | 2.1 | 1,890 | 300 | 0 |
| Bag | 3 | 91% | $4.56 \times 10^8$ | 9.1 | 3,700 | 123 | 17.4 |
| High Density Static | 7 | 89% | $4.32 \times 10^8$ | 10.0 | 3,400 | 86 | 18.6 |
| Dot Matrix | 0 | 90% | $9.0 \times 10^8$ | 2.1 | 1,890 | 300 | 0 |
| Bag | 3 | 89% | $5.5 \times 10^8$ | 12.6 | 6,930 | 278 | 2.1 |
|  | 7 | 85% | $7.8 \times 10^8$ | 39.9 | 29,400 | 260 | 3.7 |
|  | 10 | 88% | $9.7 \times 10^8$ | 32.0 | 31,000 | 164 | 7.2 |
|  | 14 | 74% | $1.1 \times 10^9$ | 122.0 | 130,000 | 99 | 7.3 |

EXAMPLE 7

Cells freshly collected from a normal donor were partitioned into SteriCell TM bags (DuPont) and into a 0.45 μ Dot Matrix vessel of Example 1. The culture medium used was Aim-V (Gibco) supplemented with 10 units/ml rIL-2. Flow rate in the Dot Matrix vessel was 10 ml/hr. The following data were obtained:

| Device | Days | Viability | Total Viable Cells | $LU_{30}/$ $10^6$ Cells | Total Lytic Units | Glucose [mg/dl] | Lactate [mMolar] |
|---|---|---|---|---|---|---|---|
| SteriCell TM | 0 | 95% | $1.0 \times 10^8$ | 0.0 | 0 | 300 | 0 |
| Bag | 3 | 95% | $7.6 \times 10^7$ | 19.8 | 1,500 | 287 | 1.3 |
| Low Density Static Culture | 6 | 94% | $8.4 \times 10^7$ | 66.1 | 5,500 | 266 | 3.3 |
| SteriCell TM | 0 | 95% | $1.0 \times 10^9$ | 0.0 | 0 | 300 | 0 |
| Bag | 3 | 95% | $3.3 \times 10^8$ | 11.4 | 3,700 | 177 | 11.3 |
| High Density Static Culture | 6 | 96% | $7.7 \times 10^8$ | 55.2 | 42,000 | 93 | 17.2 |
| Dot Matrix | 0 | 95% | $1.0 \times 10^9$ | 0.0 | 0 | 300 | 0 |
| Bag | 3 | 95% | $4.9 \times 10^8$ | 12.2 | 5,900 | 224 | 6.2 |
|  | 6 | 95% | $6.6 \times 10^8$ | 66.5 | 43,000 | 212 | 7.6 |

EXAMPLE 8

Cells from a normal donor were placed in a 1.0 μ Dot Matrix vessel of Example 1 at a high concentration and into a static SteriCell TM bags (DuPont) at a density known to yield good LAK cell activation. Cells were cultured in Aim-V medium (Gibco). The flow rate in the Dot Matrix device was maintained at 10 ml/hr.

| Device | Days | Viability | Total Viable Cells | $LU_{30}/$ $10^6$ Cells | Total Lytic Units | Glucose [mg/dl] | Lactate [mMolar] |
|---|---|---|---|---|---|---|---|
| Dot Matrix | 0 | 100% | $5.8 \times 10^9$ | 0.0 | 0 | 300 | 0 |
| at Very High Density | 3 | 26% | $5 \times 10^7$ | 0.0 | 0 | 119 | 19.4 |
| SteriCell TM | 0 | 100% | $5.8 \times 10^8$ | 0.0 | 0 | 300 | 0 |
| Bag Static Culture | 3 | 98% | $3.7 \times 10^8$ | 28.6 | 10,000 | 250 | 5 |

The perfusable cell culture device of the present invention is commercially advantageous over currently available perfused systems. The device is not bulky, non-breakable and disposable. The flat surface of the device allows cells to spread out and stack and produces a high density of cells. The device also provides negligible shear to the cells and can be operated to allow for continuous cultivation of cells. The device is capable of acclimating to the temperature of the environment for optimal conditions and provides a sterile environment for maintenance of cells in culture. In addition, the cells can be visually examined since the device is transparent and the cells can be easily removed from the non-adherent surface of the flow divider membrane. Having described this invention in detail, those skilled in the art will appreciate numerous modifications may be made thereof without departing from the spirit of the invention. Therefore, it is not intended that the scope of this invention be limited to the specific embodiments illustrated and described. Rather, the scope is to be determined by the appended claims and their equivalents.

What is claimed is:

1. A method for expansion and maintenance of mammalian cells comprising:

(a) placing a source of mammalian cells into a perfusable cell culture device said device comprising:

(1) two liquid impermeable polymeric film sheets constructed so as to deliver oxygen and carbon dioxide at rates sufficient to maintain cells in culture joined together at their peripheral edges in a sealing manner, one of the sheets defined as an upper polymeric layer and the other defined as a lower polymeric layer;

(2) a gas and liquid permeable flow divider membrane affixed between said upper polymeric layer and said lower polymer layer and affixed to said lower polymeric layer so as to provide channels for fluid distribution with the pressure drop across the flow divider membrane being significantly greater than pressure through the channels thereby providing substantially even pressure across the flow divider area and allowing the culture medium to flow uniformly over the surface areas of the flow divider membrane;

(3) an inlet port in said lower polymeric layer through which culture medium can be introduced between said lower polymeric layer and said flow divider membrane;

(4) said upper polymeric layer and said flow divider membrane being arranged with respect to each other so as to form a chamber between said upper polymeric layer and said flow divider membrane through which growth medium can be perfused at a controlled rate uniformly across the surface of the flow divider membrane and in which cells are cultured; and (5) a port in said upper polymeric layer through which cells may be placed into the cell culture device, cultured cells may be removed from said cell culture device, and perfused nutrients may be collected from said cell culture device;

(b) perfusing said device with a cell culture medium,
(c) withdrawing spent culture medium through said port in the upper polymeric layer, and
(d) maintaining said device in an incubator.

2. A method for expansion and maintenance of mammalian cells as claimed in claim 1 wherein said mammalian cells are tumor infiltrating lymphocyte cells.

3. A method for expansion and maintenance of mammalian cells as claimed in claim 1 wherein said mammalian cells are lymphokine activated killer cells.

4. A method for expansion and maintenance of mammalian cells as claimed in claim 1 wherein said mammalian cell are hybridoma cells.

5. A method for expansion and maintenance of mammalian cells as claimed in claim 1 wherein said mammalian cells are U937 cells.

6. A method for expansion and maintenance of microbial cells comprising:

(b) placing a source of microbical cells into a perfusable cell culture device said device comprising:

(1) two liquid impermeable polymeric film sheets constructed so as to deliver oxygen and carbon dioxide at rates sufficient to maintain cells in culture joined together at their peripheral edges in a sealing manner, one of the sheets defined as an upper polymeric layer and the other defined as a lower polymeric layer;

(2) a gas and liquid permeable flow divider membrane affixed between said upper polymeric layer and said lower polymeric layer and affixed to said lower polymeric layer so as to provide channels for fluid distribution with the pressure drop across the flow divider membrane being significantly greater than pressure through the channels thereby providing substantially even pressure across the flow divider area and allowing the culture medium to flow uniformly over the surface area of the flow divider membrane;

(3) an inlet port in said lower polymeric layer through which culture medium can be introduced between said lower polymeric layer and said flow divider membrane;

(4) said upper polymeric layer and said flow divider membrane being arranged with respect to each other so as to form a chamber between said upper polymeric layer and said flow divider membrane through which growth medium can be perfused at a controlled rate uniformly across the surface of the flow divider membrane and in which cells are cultured; and (5) a port in said upper polymeric layer through which cells may be placed into the cell culture device, cultured cells may be removed from said cell culture device, and perfused nutrients may be collected from said cell culture device;

(b) perfusing said device with a cell culture medium,
(c) withdrawing spent culture medium through said port in the upper polymeric layer, and
(d) maintaining said device in an incubator.

7. A method for expansion and maintenance of insect cells comprising:

(a) placing a source of insect cells into a perfusable cell culture device said device comprising:

(1) two liquid impermeable polymeric film sheets constructed so a to deliver oxygen and carbon dioxide at rates sufficient to maintain cells in culture joined together at their peripheral edges in a sealing manner, one of the sheets defined as an upper polymeric layer and the other defined as a lower polymeric layer;

(2) a gas and liquid permeable flow divider membrane affixed between said upper polymeric layer and said lower polymeric layer and affixed to said lower polymeric layer so as to provide channels for fluid distribution with the pressure drop across the flow divider membrane being significantly greater than pressure through the channels thereby providing substantially even pressure across the flow divider area and allowing the culture medium to flow uniformly over the surface area of the flow divider membrane;

(3) an inlet port in said lower polymeric layer through which culture medium can be introduced between said lower polymeric layer and said flow divider membrane;

(4) said upper polymeric layer and said flow divider membrane being arranged with respect to each other so as to form a chamber between said upper polymeric layer and said flow divider membrane through which growth medium can be perfused at a controlled rate uniformly across the surface of the flow divider membrane and in which cells are cultured; and (5) a port in said upper polymeric layer through which cells may be placed into the cell culture device, cultured cells may be removed from said cell culture device, and perfused nutrients may be collected from said cell culture device;

(b) perfusing said device with a cell culture medium,
(c) withdrawing spent culture medium through said port in the upper polymeric layer, and
(d) maintaining said device in an incubator.

8. A method for expansion and maintenance of plant cells comprising:

(a) placing a source of plant cells into a perfusable cell culture device said device comprising:

(1) two liquid impermeable polymeric film sheets constructed so as to deliver oxygen and carbon dioxide at rates sufficient to maintain cells in culture joined together at their peripheral edges in a sealing manner, one of the sheets defined as an upper polymeric layer and the other defined as a lower polymeric layer;

(2) a gas and liquid permeable flow divider membrane affixed between said upper polymeric layer and said lower polymeric layer and affixed to said lower polymeric layer so as to provide channels for fluid distribution with the pressure drop across the flow divider membrane being significantly greater than pressure through the channels thereby providing substantially even pressure across the flow divider area and allowing the culture medium to flow uniformly over the surface area of the flow divider membrane;

(3) an inlet port in said lower polymeric layer through which culture medium can be introduced between said lower polymeric layer and said flow divider membrane;

(4) said upper polymeric layer and said flow divider membrane being arranged with respect to each other so as to form a chamber between said upper polymeric layer and said flow divider membrane through which growth medium can be perfused at a controlled rate uniformly across the surface of the flow divider membrane and in which cells are cultured; and (5) a port in said upper polymeric layer through which; cells may be placed into the cell culture device, cultured cells may be removed from said cell culture device, and perfused nutrients may be collected from said cell culture device;

(b) perfusing said device with a cell culture medium, (c) withdrawing spent culture medium through said port in the upper polymeric layer, and (d) maintaining said device in an incubator.

* * * * *